United States Patent [19]

Willis et al.

[11] Patent Number: 5,505,686
[45] Date of Patent: Apr. 9, 1996

[54] ENDOSCOPE WITH PROTRUDING MEMBER AND METHOD OF UTILIZING THE SAME

[75] Inventors: Allan F. Willis, Moorpark; Richard L. Quick, Trabuco Canyon; Hien Van Nguyen, Santa Ana; Tuoc T. Nguyen, Westminster; John P. Greelis, Aliso Viejo, all of Calif.

[73] Assignee: Imagyn Medical, Inc., Laguna Niguel, Calif.

[21] Appl. No.: 238,314

[22] Filed: May 5, 1994

[51] Int. Cl.$^6$ ............................................. A61B 1/00
[52] U.S. Cl. ........................... 600/104; 600/114; 600/127
[58] Field of Search ........................... 128/45 M, 6, 7; 600/104, 114, 117, 103, 127, 129

[56] References Cited

U.S. PATENT DOCUMENTS

| | | |
|---|---|---|
| 3,941,121 | 3/1976 | Olinger et al. . |
| 4,254,762 | 3/1981 | Yoon . |
| 4,345,589 | 8/1982 | Hiltebrandt . |
| 4,345,602 | 8/1982 | Yoshimura et al. . |
| 4,538,622 | 9/1985 | Samson et al. . |
| 4,545,390 | 10/1985 | Leary . |
| 4,682,585 | 7/1987 | Hiltebrandt . |
| 4,762,129 | 8/1988 | Bonzel . |
| 4,793,326 | 12/1988 | Ghishido ................................ 128/4 |
| 5,103,804 | 4/1992 | Abele et al. ...................... 600/104 X |
| 5,207,213 | 5/1993 | Auhll et al. . |
| 5,279,280 | 1/1994 | Bacich et al. . |
| 5,290,294 | 3/1994 | Cox et al. ........................... 600/104 X |
| 5,300,023 | 4/1994 | Lowery et al. . |

OTHER PUBLICATIONS

The Wilkerson Group, Inc., *An Assessment of Percutaneous Transluminal Coronary Angioplasty and Its Impact on Related Cardiovascular Markets.*

Primary Examiner—Richard J. Apley
Assistant Examiner—Beverly M. Flanagan
Attorney, Agent, or Firm—Donald E. Stout; Gordon L. Peterson

[57] ABSTRACT

An endoscope including an elongated endoscope body sized and adapted for insertion into a passage, such as a passage of the body of a patient. Optical components are carried by the endoscope body to enable viewing of the passage distally of the distal end of the endoscope body within a field of view of the endoscope. An elongated, resilient member is mounted on and carried by the endoscope body such that the endoscope body and the resilient member are a unitary assembly which can be inserted as a unit into the passage. The resilient member extends beyond the distal end of the endoscope body and is capable of contacting material within or forming the passage and relatively displacing the distal end of the endoscope body and such material within the field of view of the endoscope to enhance viewing of the passage with the endoscope.

39 Claims, 3 Drawing Sheets

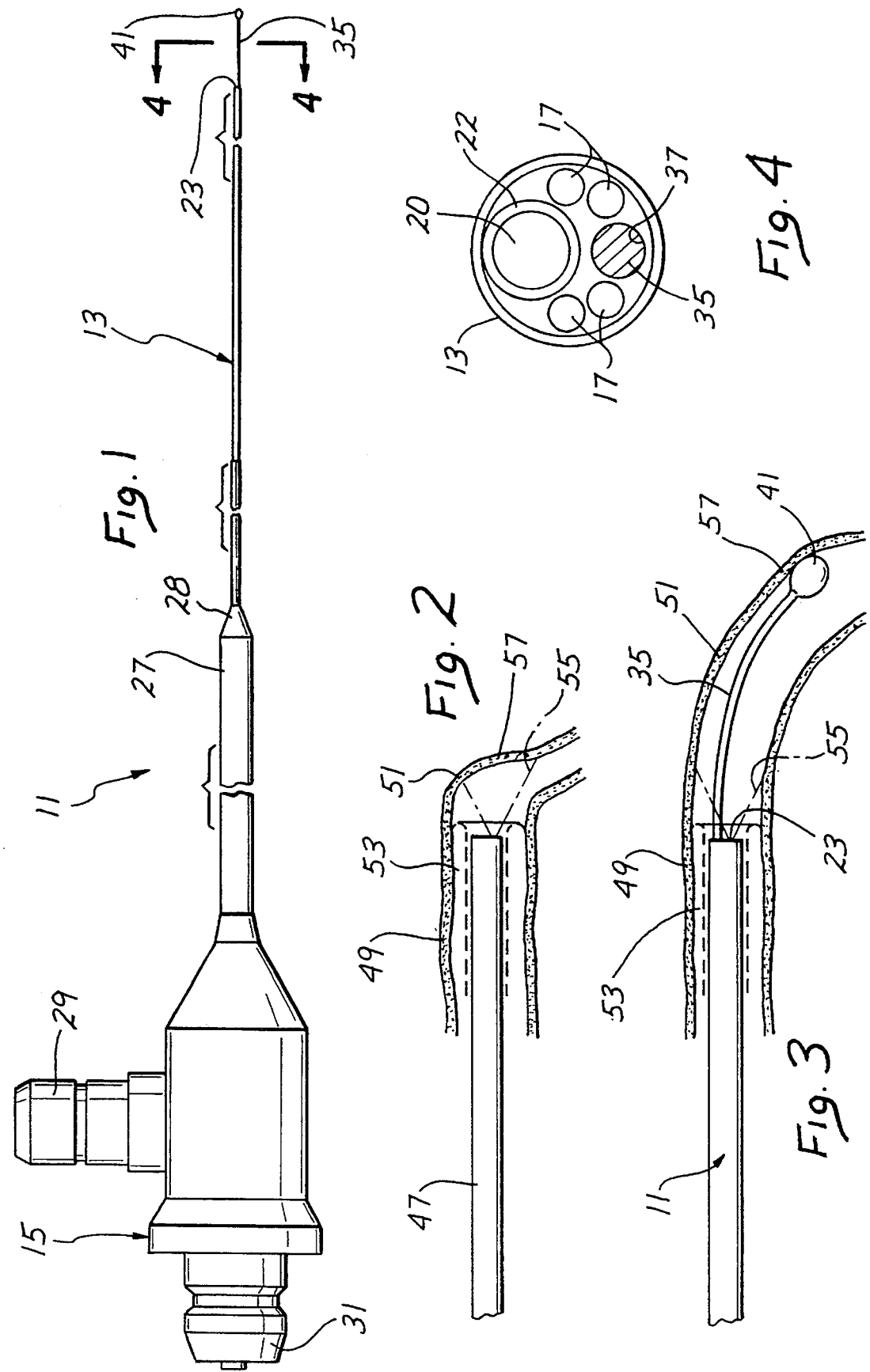

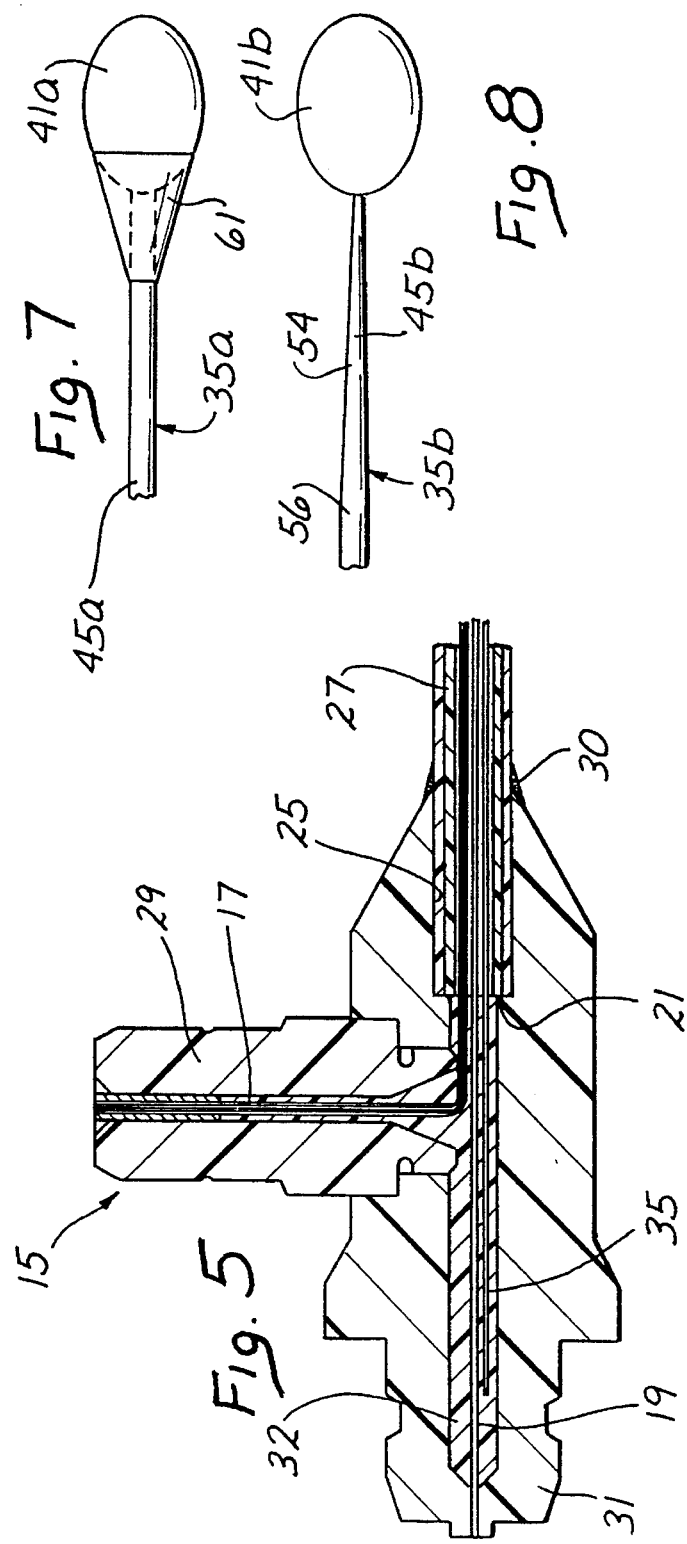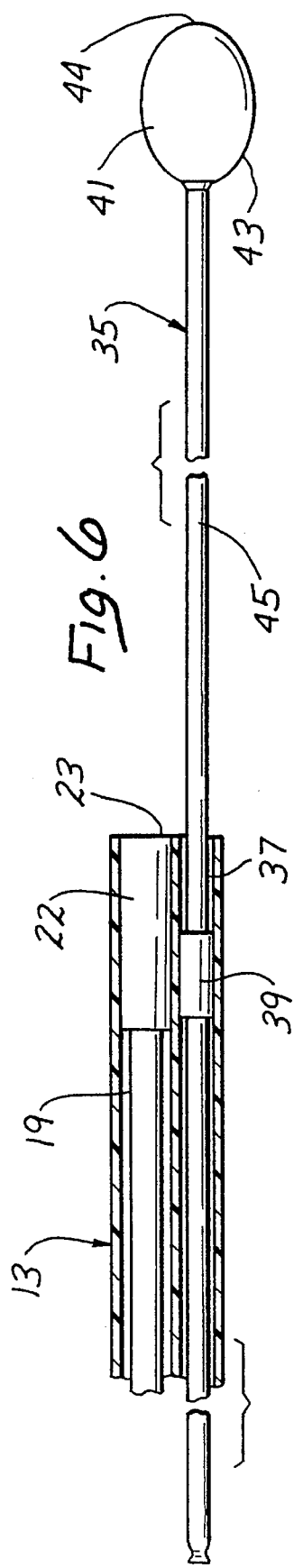

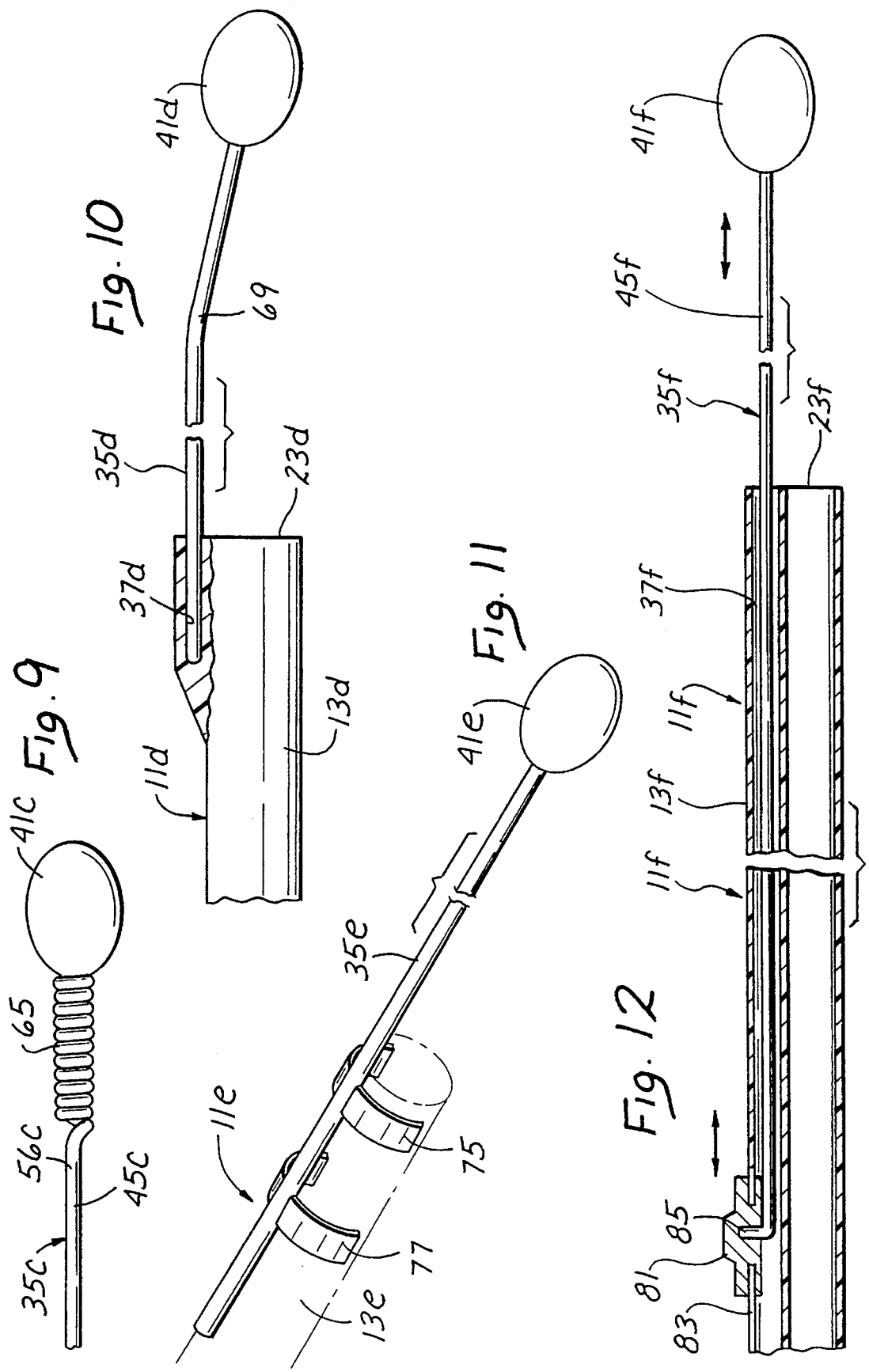

ENDOSCOPE WITH PROTRUDING MEMBER AND METHOD OF UTILIZING THE SAME

BACKGROUND OF THE INVENTION

Endoscopes are commonly used to view the interior passage of an object. An endoscope typically includes an endoscope body and optical components carried by the endoscope body to enable viewing of the passage distally of the distal end of the endoscope body and within a field of view of the endoscope. The optical components may include, for example, illumination and visualization fibers in the endoscope body for conducting light distally and an image proximally, of the endoscope body.

Endoscopes have industrial applications wherein the endoscope can be used to view a passage within, for example, industrial equipment. Endoscopes also have medical applications wherein the endoscope is used to view a passage within the body of a patient.

Medical endoscopes used for angioscopy are commonly placed in the vascular system using a guidewire. For example, the guidewire may first be placed within a blood vessel and the endoscope may have a lumen receiving the guidewire such that the endoscope can be moved along the guidewire to a desired position. It is also known to provide an angioplasty catheter, as opposed to an endoscope, with a fixed guidewire which allows the operator to track and place the catheter at the desired location in the vascular system.

One problem with these procedures is that it may be difficult to view curved, collapsed or partially collapsed portions of the passage. In addition, material within the passage may tend to obstruct viewing through the endoscope within the field of view of the endoscope.

In an effort to solve this problem, it is known to use a resectoscope for removing or ablating unwanted tissue. It is also known to use a nozzle in an attempt to spray material off the distal lens of the endoscope as shown, for example in Auhll et al U.S. Pat. No. 5,207,213. However, these techniques do not address the visualization problems posed by a curved, collapsed or partially collapsed passage and resection increases the likelihood of injury and trauma to the patient. Similarly, the use of a technique as shown for example in Hiltebrandt U.S. Pat. No. 4,682,585 for radially spacing the distal objective of the endoscope is also not effective to address these problems.

Endoscopes have also been introduced through hollow sleeves with sharpened points for puncturing the abdomen in laparoscopic procedures such as shown in Hiltebrandt U.S. Pat. No. 4,345,589 and Yoon U.S. Pat. No. 4,254,762. However, the rigidity of the hollow sleeves and their sharp tips make them unsuited for many procedures where tissue penetration is to be avoided and for passages which are curved.

SUMMARY OF THE INVENTION

This invention solves these problems. This invention enhances the viewing of a passage in which the endoscope is placed by relatively displacing the distal end of the endoscope and material within or forming the passage. This relative displacement of the distal end of the endoscope and such material may open a collapsed or partially collapsed passage, displace the distal end of the endoscope body from the wall of the passage, displace material within the passage that would otherwise obstruct the view and/or elongate a curved portion of the passage. This can be accomplished for both industrial and medical endoscopes, and in the case of medical endoscopes, it can be accomplished without increasing the likelihood of tissue penetration. The features of this invention are applicable to those endoscopes having a working channel or lumen and to those which do not.

The invention may be embodied in an endoscope which includes an elongated endoscope body having a distal end with the endoscope body being sized and adapted for insertion into a passage of an object. The object may be the body of a patient or industrial equipment. The endoscope also includes optical components carried by the endoscope body to enable viewing of the passage distally of the distal end within a field of view of the endoscope when the endoscope is in the passage.

To accomplish the desired relative displacement, the endoscope includes an elongated member mounted on, and carried by, the endoscope body such that the endoscope body and the elongated member are a unitary assembly which can be inserted as a unit into the passage. In this context, the elongated member may be either fixed longitudinally with respect to the endoscope body or mounted on the endoscope body for generally longitudinal movement relative to the endoscope body. In either event, however, the endoscope body and the elongated member are a unitary assembly which can be inserted as a unit into the passage. This unitary assembly can be contrasted with a conventional guidewire system in which a guidewire is first placed within a blood vessel and subsequently an endoscope or catheter is run over the guidewire to a desired location in the vessel.

The elongated member extends beyond the distal end of the endoscope body and is capable of contacting material within or forming the passage. The elongated member can relatively displace the distal end of the endoscope body and such material within the field of view of the endoscope to enhance viewing of the passage with the endoscope.

For those applications in which penetration of the wall of the passage being examined would not cause a problem, the elongated member may be rigid, if desired. However, for the vast majority of medical applications and for certain industrial applications, penetration of the wall of the passage being examined is to be avoided. To greatly reduce the likelihood of penetration of the wall of the passage, the elongated member can be made resilient. The resilience of the resilient member allows it to be elastically deflected, and when the deflecting force is removed, its resilience, elasticity or memory will return it to its original unstressed position. The resilient member is flexible in the sense that it can be very easily elastically or resiliently deflected, but is not flexible in the sense of a length of string which has no memory for returning to its original position. Preferably, the resilient member is highly elastic so it can be very easily deflected. If the resilient member required substantial force to deflect, the risk of penetration of the wall of the passage would increase. Because of the large number of applications where penetration of the wall of the passage being examined is desirable, the elongated member is often referred to as a resilient member below in this specification.

For medical applications where tissue penetration is to be avoided or for any other application where penetration of the object being examined is to be avoided, the resilient member preferably terminates distally in an enlarged distal tip portion. The enlarged distal tip portion is also more capable than a smaller distal tip portion in providing a relatively wide area in radial cross section for viewing. For some medical applications, it is preferred that the distal tip portion have a maximum cross sectional area which is at least about as large as the cross sectional area of the distal end of the endoscope body. For medical applications in the fallopian tube, the maximum cross sectional dimension of the distal tip portion is preferably between about 0.15 millimeter and 1.2 millimeters. To further reduce the likelihood of tissue penetration in a medical endoscope, a region of the resilient member proximally of the distal tip portion may be made of increased flexibility and in some cases of progressively increasing flexibility as such region extends distally.

To further reduce the likelihood of tissue penetration, the resilient member is preferably very elastic such that it can be easily deflected, and when the deflecting force is removed, it will return to its normal, unrestrained position. Although various different materials can be employed, a nickel-titanium alloy is preferred because of its inherent elasticity.

The spacing between the distal tip portion and the distal end of the endoscope body can be selected depending upon the nature of the passage being examined. Further by way of example, for medical applications in the fallopian tube, the distal tip portion has a distal end which is between about 1 millimeter and 15 millimeters from the distal end of the endoscope body.

The endoscope may be either rigid or flexible depending upon the usage to which it is to be put. For medical applications, it is ordinarily preferably made flexible and sized to be received within the desired interior body region of a patient.

In one preferred embodiment, the resilient member is fixed longitudinally with respect to the endoscope body. In a preferred construction, the endoscope body has an endoscope lumen and the resilient member is received in the endoscope lumen. This has the advantage of reducing the likelihood that the resilient member will separate from the endoscope body and be left within the passage. Although the resilient member can be fixed longitudinally on the endoscope body in different ways, it is preferred to use bonding material for bonding the resilient member to the endoscope body within the endoscope lumen. Alternatively the resilient member can be fixed to the endoscope body by crimping, fasteners and/or other mechanical techniques.

In one preferred construction, the endoscope body has a proximal end and the endoscope lumen extends through the endoscope body from the proximal end to the distal end. The endoscope includes a hub coupled to the endoscope body adjacent the proximal end of the endoscope body and the resilient member extends through the endoscope lumen and into the hub. The bonding material for bonding the resilient member to the hub may be provided in the hub. If the endoscope includes illumination and visualization fibers, these fibers may extend through the endoscope body and into the hub.

Various other techniques can be employed to mount the resilient member on the endoscope body. For example, a clip-on assembly may be coupled to the resilient member for enabling the resilient member to clipped onto the exterior of the endoscope body. Similarly, the endoscope lumen may be a separate lumen near the periphery of the endoscope which does not extend for the full length of the endoscope body. In this event, longitudinal axes of the resilient member and the endoscope body are radially offset at the distal end of the endoscope body. To reduce the radial offset and bring the axes closer together, the resilient member may be deflected distally of the distal end of the endoscope body.

The resilient member may also be mounted on the endoscope body for generally longitudinal movement relative to the endoscope body. This mounting is different from the sliding of an endoscope over a prepositioned guidewire in that the resilient member and the endoscope body are, in effect, a unitary assembly which can be inserted as a unit into the passage to be viewed. In this form of the invention, the endoscope body has an endoscope lumen and the resilient member is slidably received in the endoscope lumen. The endoscope may also include a controller mounted on the endoscope body for moving the resilient member longitudinally in the endoscope lumen. The controller may include a control slide coupled to the resilient member and mounted for sliding movement on the endoscope body. Alternatively, the controller may include gears, wheels, a pull wire or other mechanical means for operating the resilient member.

Another feature of this invention is that the resilient member may be made very easily deflectable for insertion into the passage and then made appropriately resilient for use in relatively displacing the distal end of the endoscope body and the material within or forming the passage. This may be accomplished, for example, by constructing the elongated member of a material having a transition temperature and with the elongated member being more easily deflected below the transition temperature than above the transition temperature. The ease of deflection may be brought about, for example, by the elongated member being soft and malleable and therefore very easily permanently bent or deformed. Alternatively, the ease of deflection may be the result of the elongated member being more flexible below the transition temperature than above it. Certain known shape memory materials such as nickel-titanium alloys have this property of being soft, malleable and somewhat nonresilient in an austenitic state below the transition temperature and resilient in a martenistic state above the transition temperature.

The transition temperature can be at various levels depending upon the nature of the alloy selected for the elongated member. For medical applications, it may be desirable to have a transition temperature which is less than about the temperature of the interior of the human body. This enables the elongated member to be easily deflected during insertion into the body passage and thereafter more resilient when it rises above the transition temperature as a result of being within the desired region of the body passage. Of course, the transition temperature may be higher or lower and the elongated member may be heated to the transition temperature utilizing various heating devices, including direct electrical heating of the elongated member by current flowing through it, and/or by fluids or heating devices in proximity to the elongated member.

Although the endoscope of this invention can be put to many different uses, one important usage is for medical purposes in the viewing of a passage in the body of a patient. In this event, the endoscope can be advanced into the passage in the body of the patient with the resilient member extending beyond the distal end of the endoscope body when the endoscope is at a region of the passage. In those embodiments in which the resilient member is movable longitudinally relative to the endoscope body, it is only necessary that the resilient member extend beyond the distal end of the endoscope body when the endoscope body is at the desired region of the passage. The distal end of the endoscope body and the material within or forming the passage within the field of view of the endoscope are then relatively displaced utilizing the resilient member. The interior passage can then be viewed utilizing the endoscope while the distal end of the endoscope and the material are relatively displaced. At least some of the displacement of the material in the distal end of the endoscope is in a radial direction and the displacement is preferably carried out as a result of contacting the resilient member and the material. This contact may occur in whole or in part during the advancing of the endoscope into the passage. If the resilient member is movable longitudinally relative to the endoscope body, it may be moved to assist or accomplish the displacing of the material and the distal end of the endoscope. This method can be carried out in various passages of a patient, such as the vascular system, gastrointestinal tract, neural passages in the brain and epidural passages, and it is particularly adapted for viewing of the interior of a fallopian tube.

Another feature of the invention is that the resilient member can be used to at least assist in guiding the endoscope at least part way through a curve or curved portion of the passage. This is of importance when using the endoscope in a passage, such as a fallopian tube, which contains one or more curved portions.

The invention, together with additional features and advantages thereof may best be understood by reference to the following description taken in connection with the accompanying illustrative drawings.

BRIEF DESCRIPTION OF THE DRAWINGS

FIG. 1 is side elevational view of an endoscope constructed in accordance with the teachings of this invention.

FIGS. 2 and 3 are fragmentary, elevational views partially in section comparing the use of a prior art endoscope and the endoscope of this invention adjacent a curved region of a passage.

FIG. 4 is an enlarged sectional view taken generally along lines 4—4 of FIG. 1.

FIG. 5 is a fragmentary, axial sectional view through the hub and proximal regions of the endoscope body.

FIG. 6 is a fragmentary longitudinal sectional view through a distal region of the endoscope.

FIGS. 7–9 are fragmentary elevational views of a distal region of three different resilient members.

FIG. 10 is a fragmentary elevational view partially in section of a second embodiment of the invention.

FIG. 11 is a perspective view of a distal region of the endoscope of a third embodiment of the invention. The endoscope body is shown in phantom lines.

FIG. 12 is an enlarged fragmentary axial sectional view of an embodiment of the endoscope in which the resilient member is longitudinally movable.

DESCRIPTION OF THE PREFERRED EMBODIMENTS

FIG. 1 shows an endoscope 11 which generally includes an endoscope body 13 and a hub 15. The endoscope 13 also includes one or more illumination fibers 17 (four being illustrated in FIG. 4) and image or visualization fibers 19 (FIG. 6) and a GRIN lens 20 retained in a bushing 22.

The endoscope body 13 is flexible and has a proximal end 21 and a distal end 23. The proximal end 21 is received within an axial passage 25 of the hub 15 (FIG. 5). A strain relief tube 27 receives a region of the endoscope body 13 adjacent the proximal end 21 and the strain relief tube is also received within the passage 25. An adhesive 28 (FIG. 1), such as a urethane adhesive, joins the endoscope body 13 to the tube 27. The endoscope body 13 and the tube 27 are affixed to the hub 15 in any suitable manner, such as by a urethane adhesive 30.

The illumination fibers 17 extend from the distal end 23 through the full length of the endoscope body 13, into the passage 25 and through a leg 29 or illumination connector of the hub 15 which is adapted to be coupled to a light source (not shown). Similarly, the image fibers 19 extend from the distal end 23 through the full length of the endoscope body 13 into the passage 25 and into a leg 31 of the hub 15. A suitable adhesive, such as an epoxy adhesive 32 may be used to bond the ends of the fibers 17 and 19 to the legs 29 and 31, respectively. The leg 31 could be adapted for coupling to an eyepiece (not shown) to permit direct illumination or for coupling to a camera (not shown) to enable the image to be viewed on a monitor. The hub 15 may be constructed of any suitable rigid material with a polymeric material such as ABS being preferred.

The optical components of the endoscope 11 may be of any kind which will enable viewing of a passage such as an interior body region of a patient. In the embodiment illustrated in FIGS. 1–6, these optical components include the illumination fibers 17, the image fiber 19 and the GRIN lens 20 (FIG. 4) which serves as an objective lens.

As described thus far in the Description of the Preferred Embodiments, the endoscope 11 may be substantially similar to the endoscope shown and described in Bacich et al U.S. Pat. No. 5,279,280, which is incorporated by reference herein. The endoscope of this invention departs from the prior art in that it includes an elongated resilient member 35 which, in this embodiment is fixed longitudinally with respect to the endoscope body 13. The resilient member 35 extends axially or longitudinally beyond the distal end 23 of the endoscope body 13.

The endoscope body 13 has an endoscope lumen 37 (FIG. 4 and 6) and the resilient member 35 is received in the endoscope lumen. In this embodiment, the endoscope lumen 37 extends completely through the endoscope body 13 from the proximal end 21 to the distal end 23 and the resilient member extends through the endoscope lumen and into the leg 31 of the hub 15.

In this embodiment, the resilient member 35 is fixed longitudinally with respect to the endoscope body 13 by bonding material such as epoxy 39 adjacent the distal end 23 (FIG. 6) and by the epoxy 32 (FIG. 5). Although the epoxy 39 is located closely adjacent the distal end 31, the bonding of the resilient member 35 to the endoscope body 13 can occur virtually anywhere along the length of the resilient member.

The resilient member 35 terminates distally in an enlarged distal tip portion 41 (FIGS. 1 and 6). The enlarged distal tip portion 41 has a smoothly rounded peripheral surface 43 which is blunt or nonpenetrating both proximally and at a distal end 44 so as to minimize the likelihood of penetrating tissue when the endoscope 11 is advanced or retracted within a passage. For example, the distal tip portion 41 may spherical or generally egg-shaped and may be constructed of a polymeric material or a metal such as stainless steel or a nickel-titanium alloy.

The resilient member also includes an elongated highly elastic strand or wire 45 which makes up substantially the full length of the resilient member. In this embodiment, where high elasticity is desired, the wire 45 is constructed of a nickel-titanium alloy. The elasticity of the wire 45 makes the resilient member 35 highly flexible and easily deflected, but it will also enable the deflected resilient member to return to its natural or unstressed shape when the deflecting force is removed. The wire 45 preferably, although not necessarily, has a lubricous exterior surface. The lubricous surface may be provided in various ways such as by impregnation of a lubricous material such as polytetrafluoroethylene or by a lubricous coating of polytetrafluoroethylene, silicone oil, silicone wax or other suitable lubricous materials. The distal tip portion 41 may be a member separate from the wire 45 and attached to the wire or it may be an integrally enlarged portion of the wire 45.

In this embodiment, the endoscope 11 is flexible and is sized to be received within an interior body region of a patient. More specifically, the endoscope 11 is adapted to be used in a fallopian tube, and as such, the distal tip portion 41 preferably has a maximum cross sectional area which is at least about as large as the cross sectional area of the distal end 23 of the endoscope body 13. In one preferred construction for fallopian tube use the distal tip portion 41 preferably has a maximum cross sectional dimension which is about 0.6 millimeter. In addition, in this preferred construction the distal end 44 of the distal tip portion 41 is about 6 millimeters from the distal end 23 of the endoscope body 13.

FIG. 2 shows the use of a conventional endoscope 47 being used to view the interior of a fallopian tube 49 having a curved portion 51. The conventional endoscope 47 is delivered to a location within the fallopian tube 49 by an everting catheter 53 which may be of the type shown and described in Lowery et al U.S. Pat. No. 5,300,023 which is incorporated by reference herein. As shown in FIG. 2, the endoscope 47 has a field of view 55 which is obstructed by a wall 57 of the curved portion 51.

FIG. 3 illustrates the endoscope 11 of this invention delivered via a transvaginal route to the same region of the fallopian tube 49 by the everting catheter 53. More specifically, the endoscope 11 is advanced into the fallopian tube 49 in the body of a patient with the elongated resilient member 35 extending beyond the distal end 23 of the endoscope body when the endoscope is at the desired region of the fallopian tube. In advancing to the position of FIG. 3, the distal tip portion 41 of the resilient member 35 contacts the wall 57 of the curved portion 51 and relatively displaces the distal end 23 of the endoscope and wall 57. Consequently, the field of view 55 is materially less obstructed by the wall 57 of the curved portion 51 than in the prior art form shown in FIG. 2. The fallopian tube 49 can then be viewed utilizing the endoscope 11 while the distal end 23 of the endoscope body and the wall 57 are relatively displaced. At least some of the displacement of the wall 57 relative to the distal end of the endoscope body is in a radial direction. The contact between the distal tip portion 41 and wall 57 may occur during advancing or retracting of the endoscope 11 and while the endoscope is stationary within the fallopian tube 49. Because of the enlarged and rounded nature of the peripheral surface 44, the distal tip portion is unlikely to penetrate or damage the tissue of the fallopian tube. FIG. 3, which is somewhat schematic in nature, may also be considered as illustrating the use of the endoscope 11 in other body passages such the gastrointestinal tract, a passage of the vascular system, a neural passage or an epidural passage. Also if it is desired to move the endoscope 11 through the curved portion 51, the resilient member 35 serves, in effect, as a fixed guidewire to guide the endoscope through the curved portion.

FIG. 7 shows a distal region of a resilient member 35a which may be identical to the resilient member 35 in all respects not shown or described herein. Portions of the resilient member 35a corresponding to portions of the resilient member 35 are designated by corresponding reference numerals follows by the letter "a". The only difference between the resilient members 35 and 35a is that the latter has a fillet 61 of epoxy or other suitable material between the wire 45a and the enlarged distal tip portion 41a. The fillet 61 tapers as it extends proximally, i.e. is of progressively reducing cross sectional area as it extends proximally so as to minimize trauma to body tissue as the endoscope of which the resilient member 35a forms a part is retracted.

FIGS. 8 and 9 show resilient members 35b and 35c, respectively, each having a region immediately proximal of the distal tip portion which is of greater flexibility than a zone of the resilient member immediately proximal to such region. In FIG. 8 such region is of progressively increasing flexibility as such region extends distally. In FIG. 8, this is accomplished by progressively reducing the diameter of a region 54 of the wire 45b as the wire extends distally toward the distal tip portion 41b. The region 54 is of smaller diameter than a zone 56 immediately proximal to such region, and such region terminates at the distal tip portion 41a. In FIG. 9, increased flexibility is accomplished by winding the wire 45c into a coil 55 which terminates at the enlarged distal tip portion 41c and which is contiguous an unwound zone 56c of the wire 45c. In all other respects, the resilient members 35b and 35c may be identical to the resilient member 35. The resilient members 35a, 35b and 35c of FIGS. 7–9 can be used with any of the endoscopes of FIGS. 1 and 10–12.

FIG. 10 shows an endoscope 11d which is identical to the endoscope 11 in all respects not shown or described herein. Portions of the endoscope 11d corresponding to portions of the endoscope 11 are designed by corresponding reference numerals followed by the letter "d". The endoscope 11d differs from the endoscope 11 in that the endoscope lumen 37d is formed outside of the tube forming the endoscope body 13d, and thus the axes of the resilient member and the endoscope body 13d are radially offset at the distal end 23d of the endoscope body more than at that location in the endoscope 11. Another difference is that the resilient member 35d has a bend portion 69 distally of the distal end 23d of the endoscope body 13d so as to deflect the resilient member to bring the longitudinal axes of the resilient member closer together and to bring the distal tip portion 41d more into alignment with the axis of the endoscope body. In this embodiment, this deflection is sufficient so as to make the distal tip portion 41d almost directly in front of the endoscope body 13d. Of course, the degree of bending at the bend portion 69 can be varied as desired.

FIG. 11 shows an endoscope 11e which may be identical to the endoscope 11 in all respects not shown or described herein. Portions of the endoscope 11e corresponding to portions of the endoscope 11 are designated by corresponding reference numerals followed by the letter "e". A primary difference between the endoscopes 11 and 11e is that the latter includes a clip-on assembly 73 in the form of two snap-on clamps 75 and 77 for enabling the resilient member 35e to be clipped onto, and unclipped from, the exterior of the endoscope body 13e. The clamps 75 and 77 are resilient and extend more than half way around the endoscope body 13e. The embodiment of FIG. 11 enables a conventional endoscope to be converted so as to embody the features of this invention. The clamps 75 and 77 fixedly attach the resilient member 35e to the endoscope body 13e.

FIG. 12 shows an endoscope 11f which is identical to the endoscope 11 in all respects not shown or described herein. Portions of the endoscope 11f corresponding to portions of endoscope 11 are designated corresponding reference numerals followed by the letter "f". The primary difference between the endoscopes 11 and 11*f* is that in the endoscope 11*f*, the resilient member 35*f* is mounted on the endoscope body 13*f* for generally longitudinal movement relative to the endoscope body. In this embodiment, the resilient member 35*f* is slidably received in the endoscope lumen 37*f* and the endoscope includes a controller in the form of a control slide 81 mounted on the endoscope body for moving the resilient member longitudinally in the endoscope lumen. The endoscope lumen 37*f* opens at the distal end 23*f* of the endoscope body 13*f*. The control slide 81 is mounted for sliding movement in a slot 83 in the endoscope body 13*f*. The proximal end portion of the resilient member 35*f* is bent to form a tab 85 which is received in, and attached to, the control slide 81. The resilient member 35*f* can be moved longitudinally relative to the endoscope body 13*f* by moving the control slide 81 back and forth in the slot 83.

All of the embodiments of the invention can be used in the same manner as described above in connection with FIG. 3 for the endoscope 11. In addition, with the endoscope 11*f*, the resilient member 35*f* can be moved longitudinally relative to the endoscope body 13*f* during longitudinal movement of the endoscope body 13*f* or while the endoscope body is stationary to bring about relative displacement between the resilient member and any material, such as the wall 57 (FIG. 3), which is to be engaged and moved relative to the end portion 23*f* of the endoscope body. For example, the endoscope body 13*f* could be allowed to remain stationary in the fallopian tube 49 while the resilient member 35*f* is moved back and forth until a desired view of the interior of the fallopian tube is obtained.

Although the invention has been described with reference to an endoscope for medical use and particularly an endoscope for viewing of the fallopian tube, the features of this invention are applicable to industrial uses such as the viewing of passages of machinery and equipment.

An optional feature of the invention which is applicable to all of the embodiments described above is to construct the elongated member 35 (FIG. 1) of a nickel-titanium alloy which has a transition temperature such that the resilient member is more easily deflected below the transition temperature than above the transition temperature. For example, below the transition temperature with the elongated member in an austenitic state, it would be soft, malleable and somewhat non-resilient. Above the transition temperature in the martenistic state, the resilient member 35 is resilient. The transition temperature may be slightly less than the temperature of the interior of the human body. Consequently, when the endoscope 11 is transvaginally introduced into the fallopian tube 49, the resilient member 35 is below the transition temperature as a result of being within the everting catheter 53 and therefore insulated from the patient's body. However, by advancing the endoscope, and in particular the resilient member 35 distally so as to place the resilient member in the fallopian tube outside of the everting catheter 53, it will be heated by the patient's body to above the transition temperature and assume its desired resilient state for use in viewing, and if desired movement through, the fallopian tube.

Although exemplary embodiments of the invention have been shown and described, many changes, modifications and substitutions may be made by one having ordinary skill in the art without necessarily departing from the spirit and scope of this invention.

We claim:

1. An endoscope comprising:

an elongated endoscope body having a distal end, said endoscope body being sized and adapted for insertion into a passage of an object;

optical components carried by the endoscope body to enable viewing of the passage distally of the distal end within a field of view of the endoscope when the endoscope is in the passage;

an elongated, resilient member mounted on and carried by the endoscope body such that the endoscope body and the resilient member are a unitary assembly which can be inserted as a unit into the passage;

said resilient member extending beyond the distal end of the endoscope body and being capable of contacting material within or forming the passage and relatively displacing the distal end of the endoscope body and such material within the field of view of the endoscope to enhance viewing of the passage with the endoscope;

the endoscope body having an endoscope lumen and the resilient member being slidably received in said endoscope lumen;

the endoscope including a controller mounted on the endoscope body for moving the resilient member longitudinally in said endoscope lumen; and the controller including a control slide coupled to the resilient member and mounted for sliding movement on the endoscope body.

2. An endoscope as defined in claim 1 wherein the resilient member terminates distally in an enlarged distal tip portion.

3. An endoscope as defined in claim 1 wherein the endoscope lumen opens at the distal end of the endoscope body and the resilient member terminates distally in an enlarged distal end portion.

4. An endoscope as defined in claim 1 wherein the resilient member has a lubricous exterior surface.

5. An endoscope comprising:

an elongated endoscope body having a distal end, said endoscope body being sized and adapted for insertion into a passage of an object;

optical components carried by the endoscope body to enable viewing of the passage distally of the distal end within a field of view of the endoscope when the endoscope is in the passage;

an elongated, resilient member mounted on the endoscope body, said resilient member being fixed longitudinally with respect to the endoscope body;

said resilient member extending beyond the distal end of the endoscope body and being capable of contacting material within or forming the passage and relatively displacing the distal end of the endoscope body and such material within the field of view of the endoscope to enhance viewing of the passage with the endoscope;

the endoscope body having an endoscope lumen and said resilient member being received in said endoscope lumen; and bonding material for bonding the resilient member to the endoscope body within the endoscope lumen.

6. An endoscope as defined in claim 5 wherein the endoscope body has a proximal end and the endoscope lumen extends through the endoscope body from the proximal end to the distal end, the endoscope includes a hub coupled to the endoscope body adjacent the proximal end of the endoscope body, and the resilient member extends through the endoscope lumen and into said hub.

7. An endoscope as defined in claim 6 including bonding material in the hub for bonding the resilient member to the hub.

8. A method of viewing an interior passage in the body of a patient with an endoscope which has an elongated endoscope body with a distal end, said method comprising:

advancing the endoscope into the passage in the body of the patient with the endoscope having a field of view and an elongated resilient member which extends beyond the distal end of the endoscope body when the endoscope is at a region of the passage;

relatively displacing the distal end of the endoscope body and material within or forming the passage within the field of view of the endoscope utilizing the resilient member; and viewing the interior passage utilizing the endoscope while the distal end of the endoscope body and said material are relatively displaced.

9. A method as defined in claim 8 wherein at least some of the displacement of the material and the distal end of the endoscope body is in a radial direction.

10. A method as defined in claim 8 wherein the step of displacing includes contacting the resilient member and the material.

11. A method as defined in claim 10 wherein the step of contacting is carried out during the step of advancing.

12. A method as defined in claim 8 wherein the passage has a curve, the resilient member extends beyond the distal end of the endoscope body when the endoscope is near the curve and including using the resilient member to at least assist in guiding the endoscope at least part way through the curve during the step of advancing.

13. A method as defined in claim 8 wherein the interior passage is a fallopian tube.

14. A method as defined in claim 8 including moving the resilient member longitudinally relative to the endoscope body during the step of displacing.

15. A method as defined in claim 8 wherein the interior passage is the gastrointestinal tract.

16. A method as defined in claim 8 wherein the interior passage is a passage in the vascular system.

17. A method as defined in claim 8 wherein the interior passage is a neural passage.

18. A method as defined in claim 8 wherein the interior passage is an epidural passage.

19. A method as defined in claim 8 wherein the resilient member has a transition temperature, the resilient member loses at least some of its resilience below the transition temperature and becomes more easily deflectable and including heating the resilient member above the transition temperature such that the resilient member is above the transition temperature at least when the endoscope is at said region of the passage.

20. An endoscope comprising:

an elongated endoscope body having a distal end, said endoscope body being sized and adapted for insertion into a passage of an object;

optical components carried by the endoscope body to enable viewing of the passage distally of the distal end within a field of view of the endoscope when the endoscope is in the passage;

an elongated member mounted on and carried by the endoscope body such that the endoscope body and the elongated member are a unitary assembly which can be inserted as a unit into the passage;

said elongated member extending beyond the distal end of the endoscope body and being capable of contacting material within or forming the passage and relatively displacing the distal end of the endoscope body and such material within the field of view of the endoscope to enhance viewing of the passage with the endoscope;

the elongated member having a transition temperature and the elongated member being more easily deflectable below the transition temperature than above the transition temperature.

21. An endoscope as defined in claim 20 wherein the elongated member is fixedly mounted on the endoscope body.

22. An endoscope as defined in claim 20 wherein the elongated member is mounted on the endoscope body for generally longitudinal movement relative to the endoscope body.

23. An endoscope as defined in claim 20 including a clip-on assembly coupled to the elongated member for enabling the elongated member to be clipped onto the exterior of the endoscope body.

24. An endoscope as defined in claim 20 wherein the elongated member terminates distally in an enlarged distal tip portion.

25. An endoscope as defined in claim 24 wherein the distal tip portion has a maximum cross sectional area which is at least about as large as the cross sectional area of the distal end of the endoscope body.

26. An endoscope as defined in claim 20 wherein the endoscope body has an endoscope lumen and the elongated member is slidably received in said endoscope lumen and wherein the endoscope includes a controller mounted on the endoscope body for moving the elongated member longitudinally in said endoscope lumen.

27. An endoscope comprising:

an elongated endoscope body having a distal end, said endoscope body being sized and adapted for insertion into a passage of an object;

optical components carried by the endoscope body to enable viewing of the passage distally of the distal end within a field of view of the endoscope when the endoscope is in the passage;

an elongated member mounted on and carried by the endoscope body, said elongated member having a transition temperature, said elongated member being more easily deflected below said transition temperature then above said transition temperature; and said elongated member extending beyond the distal end of the endoscope body and being capable of contacting material within or forming the passage and relatively displacing the distal end of the endoscope body and such material within the field of view of the endoscope to enhance viewing of the passage with the endoscope.

28. An endoscope as defined in claim 27 wherein the transition temperature is less than about the temperature of the interior of the human body.

29. An endoscope as defined in claim 27 wherein the elongated member is soft and malleable below the transition temperature and resilient above the transition temperature.

30. An endoscope comprising:

an elongated endoscope body having a distal end, said endoscope body being sized and adapted for insertion into a passage of an object;

optical components carried by the endoscope body to enable viewing of the passage distally of the distal end within a field of view of the endoscope when the endoscope is in the passage;

an elongated, resilient member mounted on and carried by the endoscope body such that the endoscope body and the resilient member are a unitary assembly which can be inserted as a unit into the passage;

said resilient member extending beyond the distal end of the endoscope body and being capable of contacting material within or forming the passage and relatively displacing the distal end of the endoscope body and such material within the field of view of the endoscope to enhance viewing of the passage with the endoscope; and a region of the resilient member proximally of the distal tip portion being of greater flexibility than a zone of the resilient member immediately proximal to such region, said zone and said region being distal of the endoscope body.

31. An endoscope as defined in claim 30 wherein said region and said zone of the resilient member proximally of the distal tip portion are of progressively increasing flexibility as such region and zone extend distally.

32. An endoscope comprising:

an elongated endoscope body having a distal end, said endoscope body being sized and adapted for insertion into a passage of an object;

optical components carried by the endoscope body to enable viewing of the passage distally of the distal end within a field of view of the endoscope when the endoscope is in the passage;

an elongated, resilient member mounted on the endoscope body, said resilient member being fixed longitudinally with respect to the endoscope body;

said resilient member extending beyond the distal end of the endoscope body and being capable of contacting material within or forming the passage and relatively displacing the distal end of the endoscope body and such material within the field of view of the endoscope to enhance viewing of the passage with the endoscope;

the endoscope being flexible and sized to be received within an interior body region of a patient, the resilient member terminating distally in an enlarged distal tip portion; and the distal tip portion having a maximum cross sectional dimension which is between about 0.15 millimeter and 1.2 millimeters.

33. An endoscope comprising:

an elongated endoscope body having a distal end, said endoscope body being sized and adapted for insertion into a passage of an object;

optical components carried by the endoscope body to enable viewing of the passage distally of the distal end within a field of view of the endoscope when the endoscope is in the passage;

an elongated, resilient member mounted on the endoscope body, said resilient member being fixed longitudinally with respect to the endoscope body;

said resilient member extending beyond the distal end of the endoscope body and being capable of contacting material within or forming the passage and relatively displacing the distal end of the endoscope body and such material within the field of view of the endoscope to enhance viewing of the passage with the endoscope, the endoscope being flexible and sized to be received within an interior body region of a patient, the resilient member terminating distally in an enlarged distal tip portion; and the distal tip portion having a distal end which is between about 1 millimeter and 15 millimeters from the distal end of the endoscope body.

34. An endoscope comprising:

an elongated endoscope body having a distal end, said endoscope body being sized and adapted for insertion into a passage of an object;

optical components carried by the endoscope body to enable viewing of the passage distally of the distal end within a field of view of the endoscope when the endoscope is in the passage;

an elongated, resilient member mounted on the endoscope body, said resilient member being fixed longitudinally with respect to the endoscope body;

said resilient member extending beyond the distal end of the endoscope body and being capable of contacting material within or forming the passage and relatively displacing the distal end of the endoscope body and such material within the field of view of the endoscope to enhance viewing of the passage with the endoscope;

the endoscope being flexible and sized to be received within an interior body region of a patient, the resilient member terminating distally in an enlarged distal tip portion; and the resilient member being constructed of a nickel-titanium alloy.

35. An endoscope comprising:

an elongated endoscope body having a distal end, said endoscope body being sized and adapted for insertion into a passage of an object;

optical components carried by the endoscope body to enable viewing of the passage distally of the distal end within a field of view of the endoscope when the endoscope is in the passage;

an elongated, resilient member mounted on and carried by the endoscope body such that the endoscope body and the resilient member are a unitary assembly which can be inserted as a unit into the passage;

said resilient member extending beyond the distal end of the endoscope body and being capable of contacting material within or forming the passage and relatively displacing the distal end of the endoscope body and such material within the field of view of the endoscope to enhance viewing of the passage with the endoscope;

said resilient member terminating distally in an enlarged distal tip portion; and the distal tip portion being permanently enlarged to have a maximum cross sectional area which is at least about as large as the cross sectional area of the distal end of the endoscope body.

36. An endoscope as defined in claim 35 wherein the resilient member is fixedly mounted on the endoscope body.

37. An endoscope as defined in claim 1 wherein the resilient member is mounted on the endoscope body for generally longitudinal movement relative to the endoscope body.

38. An endoscope as defined in claim 35 including a clip-on assembly coupled to the resilient member for enabling the resilient member to be clipped onto the exterior of the endoscope body.

39. An endoscope as defined in claim 35 wherein the resilient member and the endoscope body have longitudinal axes which are radially offset at the distal end of the endoscope body and the resilient member is deflected distally of the distal end of the endoscope body to bring the axes of the resilient member and the endoscope body closer together.

* * * * *